US009671416B2

(12) United States Patent
Giovanoli (10) Patent No.: US 9,671,416 B2
(45) Date of Patent: Jun. 6, 2017

(54) SAMPLE PROCESSING SYSTEM FOR PROCESSING BIOLOGICAL SAMPLES (71) Applicant: HAMILTON BONADUZ AG, Bonaduz (CH)

(72) Inventor: Nando Giovanoli, Bivio (CH)

(73) Assignee: Hamilton Bonaduz Ag, Bonaduz (CH)

( * ) Notice: Subject to any disclaimer, the term of this patent is extended or adjusted under 35 U.S.C. 154(b) by 0 days.

(21) Appl. No.: 14/390,111

(22) PCT Filed: May 23, 2013

(86) PCT No.: PCT/EP2013/060693
§ 371 (c)(1),
(2) Date: Oct. 2, 2014

(87) PCT Pub. No.: WO2013/174961
PCT Pub. Date: Nov. 28, 2013

(65) Prior Publication Data
US 2015/0153369 A1    Jun. 4, 2015

(30) Foreign Application Priority Data
May 24, 2012 (DE) .................. 10 2012 208 707

(51) Int. Cl.
*G01N 35/10* (2006.01)
*G01N 35/00* (2006.01)
(Continued)

(52) U.S. Cl.
CPC ....... *G01N 35/0099* (2013.01); *B01F 9/0016* (2013.01); *B01F 9/10* (2013.01);
(Continued)

(58) Field of Classification Search
CPC ......... G01N 35/0099; G01N 35/00732; G01N 2035/0405; G01N 2035/00524; G01N 2035/00752
See application file for complete search history.

(56) References Cited

U.S. PATENT DOCUMENTS 4,845,025 A     7/1989 Lary et al.
6,656,724 B1 * 12/2003 Heimberg .......... G01N 35/0099
                                                                  422/561
(Continued)

FOREIGN PATENT DOCUMENTS

CN      201323055 Y     10/2009
CN      101568386 A      3/2012
(Continued)

OTHER PUBLICATIONS

Notice of Reasons for Rejection cited in Japanese Application No. 2015-502387 dated Sep. 7, 2015, 15 pgs.
(Continued)

*Primary Examiner* — Paul Hyun
(74) *Attorney, Agent, or Firm* — Rothwell, Figg, Ernst & Manbeck, P.C.

(57) ABSTRACT

The invention relates to a sample processing system and method for processing biological samples, comprising a sample processing device having: a receiving plate, which is arranged substantially horizontally in a plane; a first and second working arm, which can move relative to the receiving plate and extend substantially parallel to each other in a second direction (Y) over the receiving plate; at least one pipetting device mounted on the first working arm, which is movable in a second direction (Y) and in a third direction (Z) orthogonal in relation to the first and second direction (X, Y); at least one gripping device, mounted on the second working arm, with grippers that can be rotated around a
(Continued)

gripper axis of rotation (GA) parallel to the third direction (Z); and a control device for controlling the pipetting device and the gripping device.

18 Claims, 5 Drawing Sheets

(51) Int. Cl.
*B01F 9/00* (2006.01)
*B01F 9/10* (2006.01)
*G01N 35/04* (2006.01)

(52) U.S. Cl.
CPC ............... *G01N 35/00732* (2013.01); *G01N 2035/00524* (2013.01); *G01N 2035/00752* (2013.01); *G01N 2035/0405* (2013.01)

(56) References Cited

U.S. PATENT DOCUMENTS

| | | | |
|---|---|---|---|
| 2002/0102736 A1 | 8/2002 | Kittock et al. | |
| 2007/0258858 A1* | 11/2007 | Rasnow | G01N 35/0099 422/400 |
| 2008/0085507 A1 | 4/2008 | Stroud et al. | |
| 2010/0126286 A1 | 5/2010 | Self et al. | |

FOREIGN PATENT DOCUMENTS

| | | |
|---|---|---|
| EP | 1 407 861 A2 | 4/2004 |
| JP | 3-115857 U | 12/1991 |
| JP | 09089907 A | 4/1997 |
| JP | 2002-333450 A | 11/2002 |
| JP | 2004 028963 A | 1/2004 |
| JP | 2006-177961 A | 7/2006 |
| WO | 2006075201 A1 | 7/2006 |
| WO | 2008067844 A1 | 6/2008 |
| WO | 2010056903 A1 | 5/2010 |

OTHER PUBLICATIONS

English translation of Chinese Office Action 201380026866.3, dated Aug. 6, 2015 and Search Report dated Jul. 27, 2015, 15 pgs.

International Search Report cited in PCT/EP2013/060693 dated Jan. 3, 2014, 5 pgs.

Search Report cited in the German Priority Application No. 10 2012 208 707.9 dated Feb. 20, 2013, 4 pgs.

Office Action (with English Translation) issued in Chinese Patent Application No. 2013800268663, 21 pages (Oct. 9, 2016).

* cited by examiner

SAMPLE PROCESSING SYSTEM FOR PROCESSING BIOLOGICAL SAMPLES

CROSS REFERENCE TO RELATED APPLICATION

This application is a 35 U.S.C. 371 National Phase Entry Application from PCT/EP2013/060693, filed May 23, 2013, which claims the benefit of German Patent Application No. 10 2012 208 707.9 filed on May 24, 2012, the disclosure of which is incorporated herein in its entirety by reference.

The present invention relates to a sample processing system for processing of biological samples, in particular bodily fluids such as blood, saliva, secretions and the like or tissue samples, in particular for preparation of samples for a DNA analysis by PCR, comprising a sample processing device with a receiving plate, wherein the receiving plate (14) is arranged essentially horizontally in a plane defined by a first and a second direction (X, Y);

with a first and a second working arm, wherein the first and second working arm are movable relative to the receiving plate along the first direction (X), preferably along a first edge of the receiving plate, and wherein the first and the second working arms extend essentially in parallel with respect to each other in the second direction across the receiving plate, wherein at the first working arm at least one pipetting device is attached, which is movable in the second direction (Y) and in a third direction (Z) perpendicular to the first and the second directions, and wherein at the second working arm a gripping device is attached, which is movable in the second direction (Y) and in a third direction (Z) perpendicular to the first and the second direction, wherein grippers provided on the gripping device are rotatable around a gripper axis of rotation parallel to the third direction (Z); and with a control device for controlling the pipetting device and the gripping device;

a plurality of sample containers, which are filled with samples, in particular liquid samples, or which can be filled with samples or reagents, a plurality of pipetting tips, which can be used by means of the pipetting device, for aspirating and dispensing of sample liquid or further reagents necessary for the sample processing, such as a lysis-buffer, wherein the sample containers and the pipetting tips are arranged on the receiving plate by means of corresponding sample container carriers and pipetting tip carriers, respectively.

An example of such a sample processing system is known from WO 2010/056903 A1. Within this known sample processing system, sample container carriers, in which the sample containers are arranged in matrix form, are submitted manually on a first working plane into the sample processing device. Then, the sample containers are taken out separately from the sample container carriers by means of a robot arm, which transports a gripped sample container to a barcode reader and consecutively to a mixing device. After mixing the sample container is transported by another gripper to a holder and fixed therein such that by means of the gripper a closing cap screwed onto the sample container can be unscrewed and removed. After opening of the closing cap, the closing cap is hold by the gripper and by means of a pipetting device sample liquid is taken out of the sample container and delivered to another sample container (so-called aliquotation). After pipetting the first sample container is closed again and placed back into the sample container carrier. Consecutively, the aliquoted sample runs through further processing steps, such as heating, mixing, pipetting, with regard to the analysis to be performed. The different processing steps in this system are performed on differing planes, which overlap partly. Further, several different transport devices, such as the robot arm, the gripper and lifting devices, are necessary to move the sample container within the sample process system, in particular to differing planes and into different process stations such as mixing stations, closing stations. All together, a complicated and nested structure with many individual components results, which are necessary for only one special processing step. Further, the arrangement with different planes has the danger that in case of an exit of biological material because of a defective sampling container or a problem of opening/closing of the closures and the like all planes lying below are contaminated.

It is an object of the invention to provide a simplified sample processing system and method, through which the disadvantage of known systems can be avoided.

To this end, according to a first aspect of the invention it is proposed that the controlling device of the sample processing device is configured such that a sample liquid contained in a sample container, in particular of liquid biological material or of a mixture of at least one reagent with a biological material to be solved or dissolved, is mixed by the gripping device by rotating a sample container gripped with the grippers around the gripper axis of rotation, preferably with around 500 to 200 revolutions per minute.

The gripper device is hence not only used for transport of sample containers, as is the case for the known robot arm, but is additionally used for mixing of sample liquid, without it being necessary that to this end a specific mixing device has to be provided within the sample processing system. This simplifies the structure of the sample processing system or the sample processing device, as additional components can be saved. Further, this allows optimizing processing steps of the sample processing.

According to a second aspect it is proposed as a further development or also self-contained that at the at least one gripping device a first sensor device is attached, which is configured to detect an identification pattern attached to a sample container, in particular barcode, wherein the control device is configured to control the gripping device such that a gripped sample container is placed into a sample container carrier in a predetermined rotation position relative to a position, in which the identification pattern has been detected, such that a plurality of sample containers placed by the gripping device into the sample container carrier can be or are aligned with respect to the respective identification pattern essentially in the same manner.

Providing of a sensor device for detecting an identification pattern attached to the sample container allows further optimizing of process flows. Since the sensor device is moved together with the gripping device, it is not necessary that the sample container to be processed has to be moved to a specific position within the sample processing device to be able to read the identification pattern. In contrast, such an identification of a sample container may be performed shortly after gripping of the sample container and its take-out from the sample container carrier, while the gripping device is already moved to a position, at which a further processing step for the sample is performed. As identification pattern barcodes in its various known realizations are possible such as one-dimensional barcode, 2D-barcode and the like. Naturally, also further patterns or signs may be used as identification patter or may supplement a barcode, such as numerals, letters or the like.

As a further development it is proposed that the sample processing device comprises at least one closing device, which is configured such that a sample container accommodated in the closing device is detached from a corresponding closing element, such as a cap, stopper or the like, to open the sample container or is connected with such a closing element to close the sample container. Preferably, the closing device is formed such that it may perform the detaching of a tightly fixed closing element, in particular a screw closing element or screw cap and the fixing of such a closing element under use of the corresponding torque.

In this context it is further conceived that the control device is configured such that by the gripping device open or closed sample containers may be submitted to the closing device and may be taken out of it. To this end, the gripping device may be configured such that separated unused closed elements or used closing elements detached from the sample containers are grippable and are moved to the closing device and away from it. The gripping device may also be used to finally remove an already detached closing element from the corresponding sample container, for example in case of a screw closure, by conducting at least a part of a rotation of the closing element with respect to the sample container. Naturally, the gripping device may also in the reverse case place a closing element on the sample container during closing of a sample container and then, for example by at least a part of a revolution, generate an primary engagement between the closing element and the sample container. However, in this process it is not considered that the gripping device serves to detach a closing element under use of a high torque from its fixedly screwed position or to tighten it into a fixedly screwed position.

Preferably, the sample processing device is configured such that the at least one pipetting device is movable with respect to a sample container, contained in the closing device and opened, to be able to extract sample liquid from the corresponding sample container.

Further it is proposed that the sample processing system comprises at least one closing element carrier, by means of which unused closing elements can be or are provided on the receiving plate.

The sample processing system may further comprise a disposal container for disposing of used pipetting tips and/or used closing elements, wherein preferably the disposal container is arranged in particular hanging at a third edge of the receiving plate, which runs along the second direction. As disposal container a bag-like container made of plastic may be used, but also box-shaped containers with firm walls are conceivable.

The gripping device comprises preferably a plurality of movable grippers, which are configured such that sample containers or closing elements can be gripped from outside by means of the grippers. In a preferred embodiment four grippers are provided which are arranged along the circumferential direction distributed in 90° steps. However, also less or more than four grippers are conceivable. The grippers are preferably formed such that different types of sample containers or corresponding closing elements can be gripped, rotated and transported by them. The grippers may hence be used unchanged for the processing of different sample containers and their closing elements, such as the known containers PreserCyt® ampoules, SurePath™ ampoules or PCR Media tubes. Naturally, to allow for this, the control device is configured such that the gripping device or its grippers may be controlled such that different sample containers may be gripped by the grippers.

The sample processing system may further comprise an incubator device, which is arranged at the receiving plate and in which a plurality of sample containers may be accommodated. The incubator device allows for preparing steps, in particular for a DNA analysis, for example to be able to denature DNA-strands.

Preferably, the sample processing system comprises a loading device movable towards the receiving plate along the first direction (X), wherein the loading device is configured such that it moves pipetting tip carriers and/or closure carriers and/or sample container carriers and/or further carriers necessary for the sample processing along the second direction (Y) towards the receiving plate or away from it, wherein preferably the loading device is movable along a second edge of the receiving plate, which is opposite to the first edge. The loading device allows manual providing of carriers of every type outside of the receiving plate and hence also outside of the sample processing device and an automated in- or out-driving of carriers with pipetting tips, sample containers or closing elements.

The loading device comprises preferably a second sensor unit by means of which an identification pattern, in particular a barcode, of a pipette carrier and/or a closure carrier and/or a sample container carrier and/or a further carrier is detectable, and/or by which an identification pattern, in particular barcode, of at least one sample container accommodate in a sample container carrier is detectable. Due to this it is possible that carriers provided and filled manually may be controlled and a correct filling of the sample processing device may be controlled by means of the control device. Further, it may also be determined which types of sample container carriers have been loaded with which type of sample containers, to be, for example, able to perform the control of the gripping device according to the type of sample containers.

As a further development it is proposed that the number of pipetting devices attached to the first working arm is the same as the number of gripping devices on the second working arm, wherein the number is preferably one to four. If several pipetting devices or gripping devices are present, several sample containers may be processed simultaneously.

In an exemplary filling or configuration of the sample processing system it is conceivable that on the receiving plate along the first direction (X) in direction from the first working arm to the second working arm are arranged:
- a pipetting tip carrier with a plurality of pipetting tip frames, preferably five pipetting tip frames with 96 pipetting tips each arranged next to each other along the second direction (Y);
- preferably an incubator, in particular suitable for accommodating 24 sample containers of a specific type;
- preferably at least one closing element carrier with unused closing elements for a specific type of sample container;
- preferably a container for a reagent, in particular a lysis-buffer;
- at least one sample container carrier for a sample of a second type, preferably a plurality of sample container carriers for 24 sample containers of the second type, each;
- at least one sample container carrier for a second or third type of sample container, preferably a plurality of sample container carriers for 12 sample containers of the first type, each, or for 6 sample containers of the third type each;

a sample container carrier for sample containers of the first or the third type;

a sample container carrier for sample containers of the second type;

at least one one closing device, suitable for sample containers of the first and the third type, preferably for such closing devices next to each other along the second direction (Y).

The sample containers of the first type may for example to sure SurePath™ ampoules. As sample container of the third type PreservCyt® ampoules are considered. The PCR Media tubes may be used as sample containers of the second type. This distribution of specific sample containers to the claimed types is purely exemplarily and sample containers may also be used, which are known under other designations or trade names.

To this end, it is proposed as a further development that the sample processing system comprises at least one further closing device, configured for sample containers of the second type, preferably for such closing devices next to each other along the second direction (Y). Hence, within the sample processing system sample containers of at least two different types may be opened or closed by respective closing devices. In interrelation with the gripping device, which is able to grip, transport and rotate all types of sample containers, a flexibly usable sample processing system results, which may also be adapted too different processing methods.

Further, a processing method for biological samples, in particular bodily fluid as blood, salvia, secretions and the like or tissue samples is proposed, comprising the steps:

providing of at least one sample container carrier with at least one closed sample container containing a biological sample;

moving the at least one sample container carrier on a receiving plate of a sample processing device;

wherein the method according to the invention comprises the following steps, which are preferably performed repeatedly until each sample container has been processed:

gripping of the or a sample container with a gripping device of the sample processing device;

mixing of the sample liquid contained in the sample container, in particular of liquid biological material or of a mixture of at least one reagent with at least partially the solved biological material, by rotating the sample container with the gripping device, preferably with about 500 to 2000 revolutions per minute; and placing of the sample container at a desired position within the sample processing device by means of the gripping device for further processing.

The processing method comprises preferably the following further steps, which are preferably performed repeatedly until each sample container has been processed:

placing the sample container into a closing device;

detaching of a closing element of the sample container accommodated within the closing device by means of the closing device;

removing the detached closing element from the sample container and from the closing device by means of the gripping device; and preferably rotating the closing element by means of the gripping element after detaching by the closing device and before removing of the closing element, to cancel an engagement between the closing element and the sample container possibly effective after the detaching.

As further development it is proposed that in the processing method at least one pipetting tip carrier with unused pipetting tips is provided and that the at least one pipetting tip carrier is moved on the receiving plate of the sample processing device.

Further, the processing method may comprise the following steps, which are preferably performed repeatedly until each sample container has been processed:

collecting a pipetting tip from the pipetting tip carrier by means of a pipetting device;

aspirating a desired amount of sample liquid from a specific sample container;

dispensing the sample liquid accommodated in the pipetting tip into another, empty sample container; and disposing the used pipetting tip.

These processing steps may in particular be an aliquotation. In the process of aliquotation a partial amount to be analyzed (aliquotated part) may be taken out from the total amount of a sample contained in the sample container and be put into a further sample container, preferably by pipetting. In the process of aliquotating also only a partition of an entire sample into several samples may be performed, wherein the taken-out sample (aliquot) is not necessarily the one that is analyzed, one may also speak of a kind of portioning.

In addition it is proposed that the processing method comprises further the following steps, which are preferably performed repeatedly until each of the sample containers has been processed:

replacing of the beforehands removed used closing elements on or placing of an unused closing elements onto the sample container located within the closing device by means of the gripping device;

closing of the sample container located within the closing device by means of the closing device;

preferably rotating the closing element by means of the gripping device after the replacing by the gripping device and before the closing of the closing elements to generate after placing of the closing element a primary engagement between the closing element and the sample container;

removing the reclosed sample container on the closing device by means of the gripping device;

placing of the reclosed sample container, in particular in sample container carriers, preferably into the sample container carrier from which the sample container has been taken out.

Within the processing method the closed sample container, which comprises the biological probe, may be a sample container of a first type, wherein the method may further comprise the following steps: providing of at least one unclosed, preferably empty sample container of a second type in a corresponding sample container carrier, wherein on the sample containers of the first and the second type an identification pattern, preferably barcode, is attached and wherein always two sample containers of the first and the second type comprise an identical identification pattern.

To this end, it is proposed as a further development that during movement of the sample container carrier with the sample containers of the first and the second type the identification patterns on the single sample containers and preferably on the sample container carriers are detected and stored and wherein it is compared, whether to each sample container of the first type a sample container of the second type with identical identification pattern is present.

During placing of the sample container into the sample container carrier the identification pattern attached to the sample container may be detected by means of a sensor unit on the gripping device and the sample container may be placed in a predetermined rotation position with respect to the rotation position in which the identification pattern has been detected into the sample container carrier such that a plurality of sample containers placed by means of the gripping device into the sample container carrier are aligned with respect to their respective identification pattern essentially in the same manner.

In the processing method the empty sample container, into which the sample liquid is dispensed, may be a sample container of the second type.

Preferably, in the processing method the providing steps are performed outside of the sample processing device on a providing surface upstream of the sample processing device.

Further, the processing method may also comprise the steps: automated moving of the sample container carriers from the receiving plate of the sample processing device to the providing surface and manual takeout of the sample container carriers.

Additionally, it is proposed for the processing method that a closing element carrier with unused closing elements for sample containers is provided, in particular for sample containers of the second type.

To this end, the closing element carrier may be positioned manually on the receiving plate of the sample processing device.

The mixing of sample liquid in a sample container by means of the gripping device is preferably performed after a transport of the sample container into the region of a disposal container.

In the following, the invention will be described exemplarily and non-restrictively with respect to an embodiment.

Figure 1:
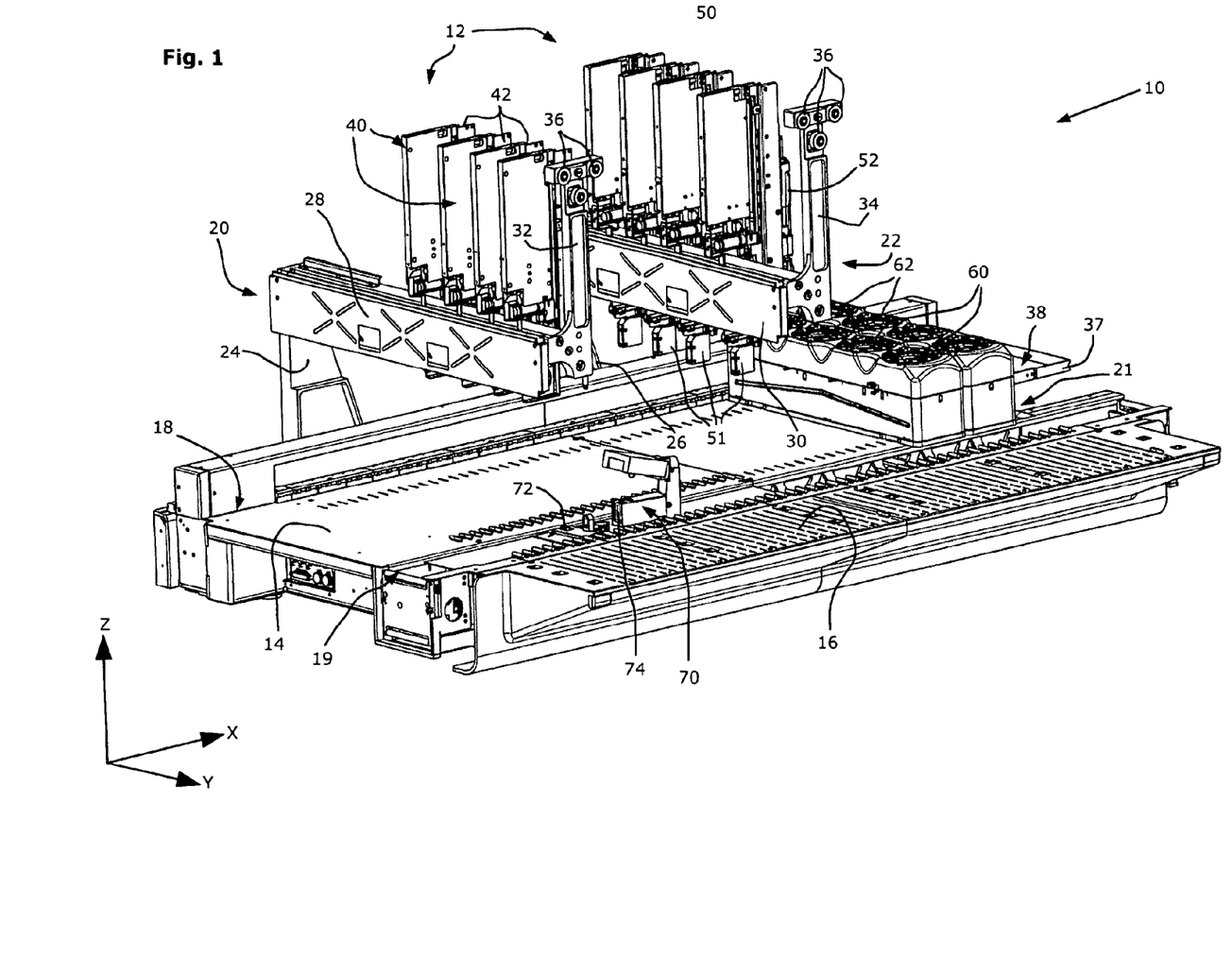
FIG. 1 shows a schematic perspective view of an embodiment of a sample processing device of a sample processing system.

FIG. 1 shows in a schematic, perspective view a sample processing system 10 with a sample processing device 12. The sample processing device 12 comprises a receiving plate 14, which is arranged via a not illustrated basic construction on a substrate. The basic construction may be connected with the sample processing device 12 or may be a separate element, such as a table or the like. The receiving plate 14 forms a plane, which extends into a first direction X and a second direction Y. Along a first edge 18 of the receiving plate two working arms 20 and 22 are arranged which are movable along the X direction. These two working arms 20, 22 are driven by not illustrated driving devices and are supported movably or rollingly such that they may be moved relative to the receiving plate 14. The working arms 20, 22 each comprise a vertical supporter 24 and 26 (partly covered) supported on the receiving plate 14 and a horizontal supporter 28 and 30 attached thereon. The horizontal supporters comprise on the ending, which is opposite to the vertical supporters 24, 26, a rolling supporter 32, 34, which points upwards into a third direction Z, which is engaged via rolls 36 with a non-illustrated guidance. The guidance is part of a not illustrated frame construction of the sample processing device 12. Such a frame construction is provided above the receiving plate 14 and may also comprise a housing with walls and openings not illustrated at this place.

On the first working arm 20 a plurality of pipetting devices 40 are arranged next to each other along its horizontal supporter 28. All pipetting devices 40 are movable with respect to the horizontal supporter 28 along the Y direction. Further, each pipetting device comprises a pipetting channel 42, which is additionally movable along the vertical Z direction. Each pipetting device may be controlled via a non-illustrated control device, such as a desktop computer or a notebook, on which a corresponding control program is installed, to be able to perform automated pipetting processes. The four pipetting devices 40 illustrated here in the example—it may also be less or more—may be controlled separately to arrive at their possible or desired positions along the horizontal supporter 28 to position a corresponding pipetting channel 42 in the Z direction and to be able to aspirate or dispense a desired amount of liquid.

On the second working arm 22 a plurality of gripping devices 50 are arranged next to each other along its horizontal supporter 30. All gripping devices 50 are movable with respect to the horizontal supporter 30 along the Y direction. Further, each gripping device 50 comprises a gripping means 52 covered in FIG. 1 (see FIG. 3), which is movable also in the vertical Z direction. Each gripping device may be controlled by means of a not illustrated control device, such as a desktop computer or notebook, on which a corresponding control program is installed, to be able to perform automated gripping processes. The four gripping devices 50 illustrated exemplarily here—it may also be less or more—may be controlled separately to arrive at their possible or desired positions along the horizontal supporter 30 and to position corresponding gripping means 52 along the Z direction.

Further, on the receiving plate 14 closing devices 60 and 62 are arranged on its right edge in FIG. 1. At a specific position in the X direction a plurality of closing devices 60 or 62 are arranged next to each other along the Y direction, in the present example four closing devices 60, 62, each. This number of arranged closing devices is only exemplarily, it may also be provided more or less closing devices 60, 62. The closing devices 60, 62 are configured to detach closures, in particular screw closures, from sample containers or to tighten them on these. To this end, the four closing devices 60 may for example be configured for a type of sample container and their closing elements (cap) and the four closing devices 62 may be provided for a different type of sample container and their closing elements (caps). The number of closing devices 60 or 62 corresponds hence to the number of pipetting devices 40 or the number of gripping devices 50 or a multiple thereof. This allows approximately synchronous processing of a number of sample containers, which corresponds to the number of pipetting devices 40 or gripping devices 50.

Along the Y direction a loading surface 16, which extends along a second edge 19 of the receiving plate 14, is arranged in front of the receiving plate 14. On this loading surface materials to be processed may be provided. By means of a loading device 70 materials arranged on respective carriers may be moved along the Y direction from the loading surface 16 to the receiving plate 14 or may be removed therefrom again. To this end, the loading device 70 comprises a carrier drive 72, which is able to engage by means of a gear wheel into a gear rod formed on a carrier (not illustrated). The loading device 70 is also movable relative to the receiving plate 14 and to the loading surface 16 along the X direction and comprises to this end a corresponding not illustrated driving unit. Further, it has to be noted that on the loading device a sensor device 74 is attached, by means of which identification patterns at the used materials, such as barcodes, may be detected, read and be transferred to the not illustrated control device. The control device is also configured to control the movements of the loading device 70 and the movements of material carriers by means of the loading device 70.

Further, on the right edge 21 of the receiving plate a frame 37 is indicated, which delimits an opening 38. On this frame 37 for example a bag of plastic may be attached as non-illustrated disposal container. Conceivable is also the arrangement of a non-flexible disposal container with firm walls (for example a box). According to the configuration of the sample processing system the disposal container may also be arranged on a position of the receiving plate 14 or the sample processing device 12, suitable for the sample processing processes.

Figure 2:
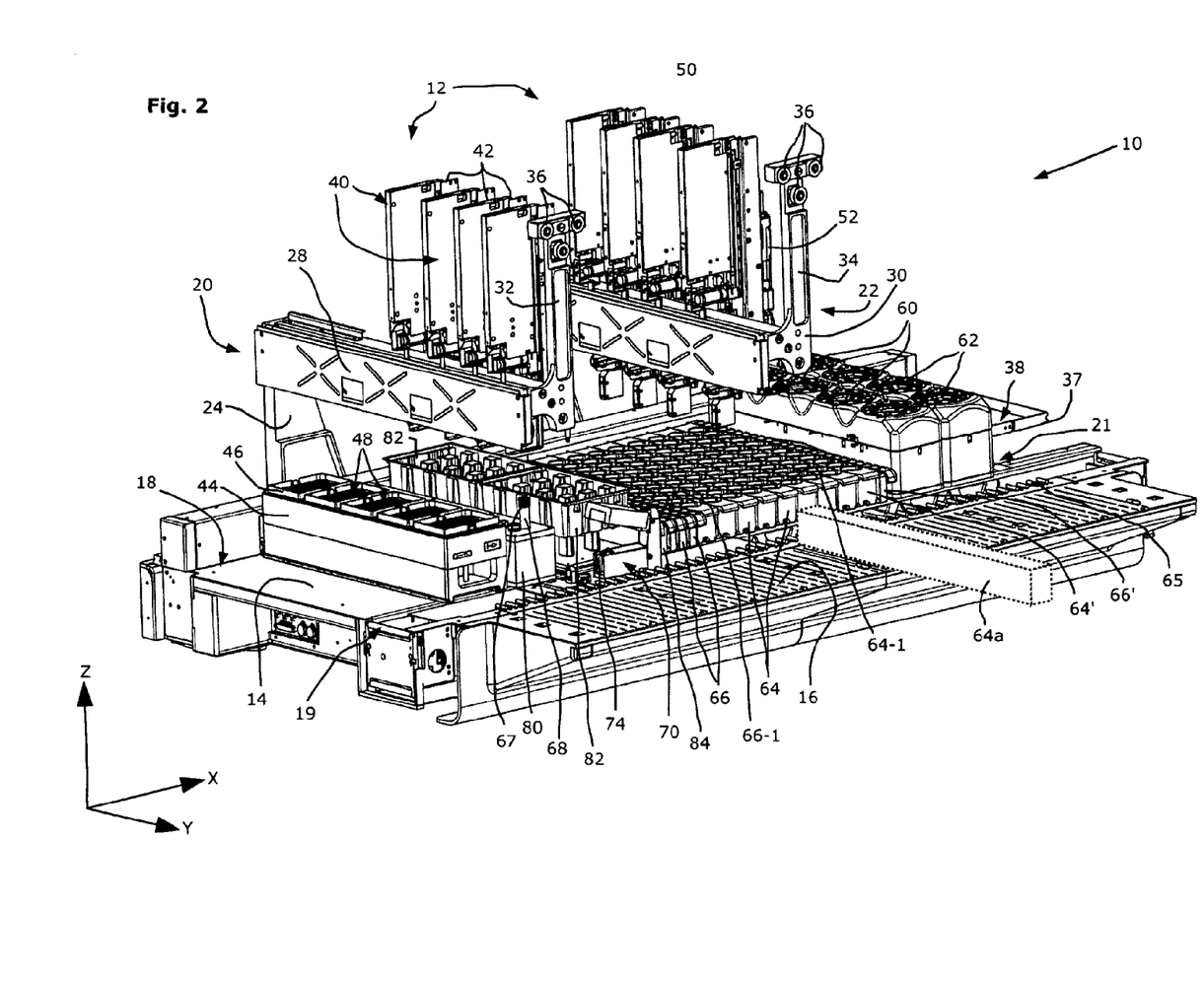
FIG. 2 shows a schematic perspective view of a possible configuration of the sample processing system with further components of the system added to the sample processing device such as sample containers and their carriers as well as pipetting tips and their carriers.

FIG. 2 shows a schematic illustration of the sample processing system 10 similar to FIG. 1, wherein on the receiving plate 14 of the sample processing device 12 further components of the sample processing system 10 are arranged in an exemplary manner. With respect to FIG. 2 on the left most a pipetting tip carrier 44 is arranged, into which a plurality of pipetting tip frames 46 is accommodated. In the respective pipetting tip frame 46 a plurality of pipetting tips 48 is arranged preferably in matrix shape. The pipetting tips 48 may be connected with the pipetting channel of a corresponding pipetting device 40 automatically to be able to perform a pipetting, i.e. aspirating and dispensing of liquid. The pipetting tip carrier 44 illustrated here may accommodate up to five pipetting tip frames 46. A pipetting tip frame comprises in the present example ninety-sixth (96) pipetting tips 48 in a 8×12 matrix arrangement. Naturally, also different pipetting tip frames with a different number of pipetting tips may be accommodated in one such pipetting tip carrier.

Figure 3:
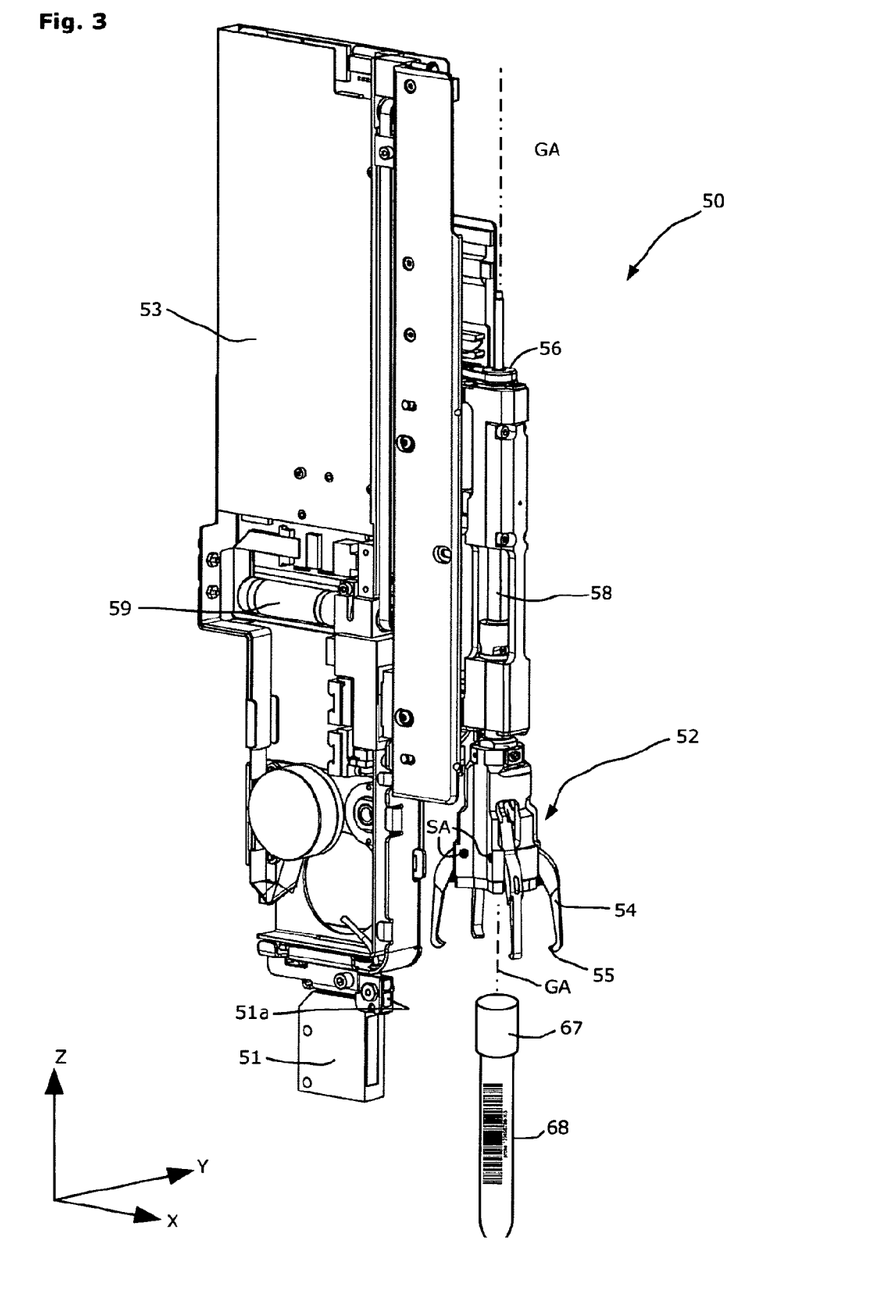
FIG. 3 shows in a schematic enlarged perspective view an embodiment of a gripping device of the sample processing device.

Carriers 64 and 66 neighboring the closing device 60 sample container on the left side are illustrated in place of a plurality of sample containers not shown in this illustration. A simplified example of a sample container 68 is illustrated in FIG. 3. As sample container the commonly known sample containers may be used, such as PreserCyt® ampoules, SurePath™ ampoules or PCR Media tubes. The illustrated example of FIG. 2 shows a configuration according to the schematic arrangement of FIG. 7. The sample container carriers 64 are here configured for sample containers 68 of a first type, such as PerserCyt® ampoules or SurePath™ ampoules. The sample containers carrier 66 are provided for sample containers 68 of a second type, such as PCR Media tubes. The sample containers of the different types have different dimensions, which is illustrated by the differently large reception openings 64-1 and 66-1 for sample containers in the sample container carriers 64, 66.

The sample processing system 10 further comprises in the illustrated configuration an incubator 80, in particular configured for sample containers of the second type. Within incubator 80 a sample container 68 is exemplarily indicated, which is closed by means of a closing element (cap, stopper) 67. The incubator is arranged next to the pipetting tip carrier 44. Next to the incubator 80 closing element carriers 82 for unused closing elements, such as screw closers, are arranged. Here, these closing element are not illustrated. Exemplarily, it is referred to the closing element illustrated in FIG. 3, which closes the sample container 68. The, in particular, stacked closing elements (caps) accommodated in the closing element carrier 82 may be provided for respective sample containers of differing types. Between the closing element carriers 82 and the first sample container carrier 66 is further a liquid container 84 arranged, in which a reagent may be comprised such as a lysis buffer or the like.

FIG. 3 shows in enlarged schematic perspective view a gripping device 50 of the sample processing system 10 or the sample processing device 12. As already mentioned the gripping device 50 comprises a gripping means 52. This gripping means 52 comprises in the present example four separate grippers or gripping arms 54, which may be swiveled around a corresponding swivel axis SA. Due to this rotatability the grippers 54, in particular their gripping sections 55, may be moved towards each other and away from each other, to grip a sample container 68 and/or a closing element 67 or to let them loose. The gripping means 52 is provided with a not-visible rotary drive to be able to rotate the gripping means 52 and the grippers 54 around a gripper axis of rotation GA. With 56 a driving device is indicated, which effects via an axle 58 connected with the gripping means the swiveling of the gripping arms 54. The whole gripping device 50, in particular also the not-visible rotary drive of the gripping means 50 and the driving device 56, are with respect to a stationary gripper basis 53 movable along the Z direction. The gripper basis 53 is arranged movably along the Y direction on the horizontal supporter 30 of the second working arm 23. The movement of the gripping means 52 along the Z direction is performed by means of a further drive 59. It should be noted that the basic structure of the gripping device, in particular its gripping basis 53, may comprise a similar or the same structure as the basic structure of a pipetting device 40.

The gripping device 50 is connected with the not illustrated control device of the sample processing system and is controlled by it. Due to the control sample container 68 or closing element 67 may be gripped and held. Further, the control device is configured to cause a rotation of the gripping means 52, wherein a gripped sample container 68 or a gripped closing element 67 are also rotated simultaneously. This may on the one hand be used for aligning of sample containers 68 and on the other hand for mixing of a sample liquid within the sample container. The mixing of sample liquid is in this process preferably performed with about 500 to 2000 revolutions of the gripping means 52 per minute.

The rotatability of the gripping means 52 allows aligning of a gripped sample container 68 such that an identification pattern 90 attached to the sample container 68, such as a barcode, may be detected by means of a sensor device 51 provided on the gripper basis 53. Therefore, it is possible to determine, which sample container 68 is processed by the gripping device 50. Further, due to this it is also possible, to bring a gripped sample container 68 in a defined rotation position with respect to a position in which the barcode of the sample container may be detected from the sensor device 51. If one takes such a position as reference, the sample container may be brought into a desired relative rotation position and be kept in this position, in order to place for example the sample container 68 in this specific rotation position into its sample container carrier 64, 66. This allows the essentially identical alignment of all sample containers 68 contained within an sample container carrier 64, 66 such that their barcodes are all pointing into the same direction, preferably in a direction, which points to the sensor device 74 of the loading device 70 (FIG. 1, 2). Hence, the sample containers 68 contained in the sensor device carrier 64, 66 or their barcodes 90 may be determined during movement of the sample container carrier 64, 66 out of the sample processing device 10. To this end, the sample container carriers 64, 66 have corresponding recesses, which make it possible to view the barcodes 90 of the sample containers 68. Therefore, the sample containers 64, 66, the single sample containers 68 or barcodes 90 present on the carriers or the containers may be determined during loading of the carriers/containers during processing of the containers and during unloading of the carriers/containers without interruption such that it is possible to ensure a correct processing.

Moreover, it is also possible that for example a sample container 68, whose barcode 90 is not aligned in the direction of the sensor device 74 of the loading device 70 during into the sample processing device 12, is gripped after loading of the sample container carrier by a gripping device 50 and that the barcode 90 of the up to now not recognized sample container may be determined later by means of the sensor device 51. It is hence possible that errors in the initial alignment of sample containers 68 in a corresponding sample container carrier 64, 66 may be automatically corrected.

In the following possible configurations of the sample processing system 10 and methods performable by means of these configurations are detailed with respect to FIGS. 4 to 7. Partly for the purpose of explanation reference signs are used, which are only contained in FIGS. 1 to 3, as the corresponding components are not illustrated in FIGS. 4 to 7.

Figure 4:
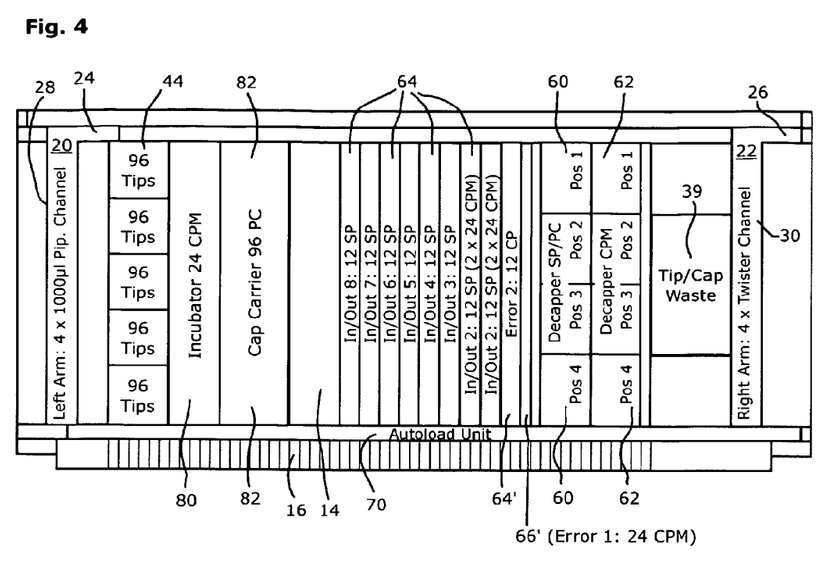
FIG. 4 shows in a schematic and simplified top view a configuration of a sample processing system for a processing method for opening/closing of sample containers of different types.

FIG. 4 shows an exemplary configuration of an automated opening/closing of sample containers by means of the closing devices 60, 62. In the illustrated configuration it is assumed that up to 8 sample container carriers 64 each with 12 sample containers of a first type, as for example of the type SurePath™ (SP) are to be opened or closed. Instead of SP sample containers also sample containers of a second type, such as PCR Media tubes (CPM) may be loaded, which are to be opened or closed. Conceivable are in particular also mixed arrangements for opening of closed sample containers, for example 72 sample containers of the first type (SP) in 6 sample container carriers 64 and 96 sample containers of the second type (CPM) in corresponding sample container carriers 66, each with 24 sample containers.

First, the sample container carriers 64, 66 are provided manually with closed sample containers at the loading surface 16. This schematically illustrated in a simplified manner by a sample container 64 illustrated by the broken lines. In this providing arrangement the different carriers 44, 64, 66 for sample containers, pipetting tips etc. are engaged with holders 65, which are arranged along the providing surface 16 in regular distances. The single sample container carriers 64, 66 are consecutively moved by means of the loading device 70 along the Y direction from the loading surface 16 to the receiving plate 14. In this process, the loading device 70 moves after each loading of a sample container carrier a bit along the X direction to be able to load the next sample container. As soon as all sample container carriers 64, 66 to be processes are loaded, the opening of the sample containers may start. To this end, the right (second) working arm 22 and the gripping device 50 attached thereon are controlled. One sample container is gripped by each gripping device 50, here exemplarily four gripping devices, and removed out of the sample container carrier 64, 66 (lifted upwardly). In this process, the barcode 90 at the respective sample container 68 may be read by means of the sensor device 51 on the gripping device 50. Consecutively, the gripped sample containers are placed into the closing device 60 in dependence of their type, in particular sample containers of the first type (SP), or in the closing device 62, in particular sample containers of the second type (CPM). The single closing devices 60, 62 detach from the sample container accommodated therein the corresponding closing element (preferably screw closure or cap). As soon as the closing elements are nearly completely detached, they may be gripped by the respective gripping devices and if necessary they may be completely screwed off, for example by one partial revolution of the gripping means 52 and the grippers 54 around the gripper axis of rotation 54. The gripped closing elements may then be removed from the sample containers and be transported to a disposal container indicated two-dimensionally by 39. As soon as the gripping device has reached a position above the disposal container 39, the closing elements may be let loose and drop into the disposal container 39. Consecutively, the gripping devices are moved again to the now opened sample containers in the respective closing devices 60, 62, in order to grip the open sample containers and to remove them from the closing devices 60, 62. The opened sample containers are hereafter placed again into a sample container carrier 64, 66, preferably each open sample container is transported to its original position, from which it has been taken out in closed state from the sample container carrier. During transportation or placing of the opened sample containers the barcode 90 provided at the sample containers may be read by using the sensor device 51, on the one hand to ensure the correct processing and on the other hand to be able to place the sample containers by movement into a specific rotation position in an aligned position into the sample container carrier, i.e. all sample containers are essentially aligned in the same manner such that their respective barcodes may be captured by the sensor device 74 of the loading device 70.

In the process of closing of open sample containers these are provided in sample container carriers 64, 66 on the loading surface 16 and loaded by means of the loading device 70. Consecutively, open sample containers are gripped by means of the gripping devices on the second working arm and placed into the closing devices 60, 62. Afterwards, the gripping devices are moved to the closing element carrier 82, on which unused closing elements are provided for the sample containers to be closed. The closing element carrier(s) have been arranged, preferably manually, beforehands within the sample processing device, i.e. on the receiving plate. The gripping devices grippe an unused closing element, each, and transport it to a corresponding open sample container within the closing devices 60, 62. By means of the gripping device the closing elements are put onto the respective sample container and preferable by means of at least one partial revolution loosely screwed onto the sample container, to allow a first engagement between the closing element and the sample container. Consecutively, the closing elements are let loose by the gripping devices such that the closing devices may tightly close the sample containers with the closing element. The then closed sample containers are taken out from the closing devices 60, 62 by means of the gripping devices and transported again to a sample container carrier. Preferably each closed sample container is transported to its original position, from which it has been taken out in open state from the sample container carrier 64, 66. During transportation or placing of the opened sample container the barcode provided at the sample containers may be read, to on the one hand ensure the correct processing and on the other hand to be able to place the sample container in aligned position within the sample container carrier, i.e. all sample containers are aligned essentially in the same manner such that their respective barcodes can be captured by the sensor device 74 of the loading device 70.

After opening or closing of all loaded sample containers, the sample container carriers 64, 66 with the completely processed sample containers (opened or closed) are moved by means of the loading device 70 from the receiving plate to the loading surface 16 (in Y direction), where they are preferably taken out manually and be delivered to processing steps, if necessary, in neighbouring further sample processing devices. It is obvious that the aforementioned steps by means of which the sample containers may be opened or closed, are performed repeatedly, since per cycle in the present example four sample containers may be processed quasi synchronously. If for example 96 sample containers are to be processed, 24 cycles with 4 sample containers have thus to be performed until a sample containers are brought from the opened to the closed state (or vice versa). Within these repeated steps performed by means of the second working arm or the gripping devices and the closing devices the method steps of loading and unloading of sample container carriers 64, 66 by means of the loading device are not included, also if the loading device naturally performs several loading or unloading processes after each other or is able to do so.

Figure 5:
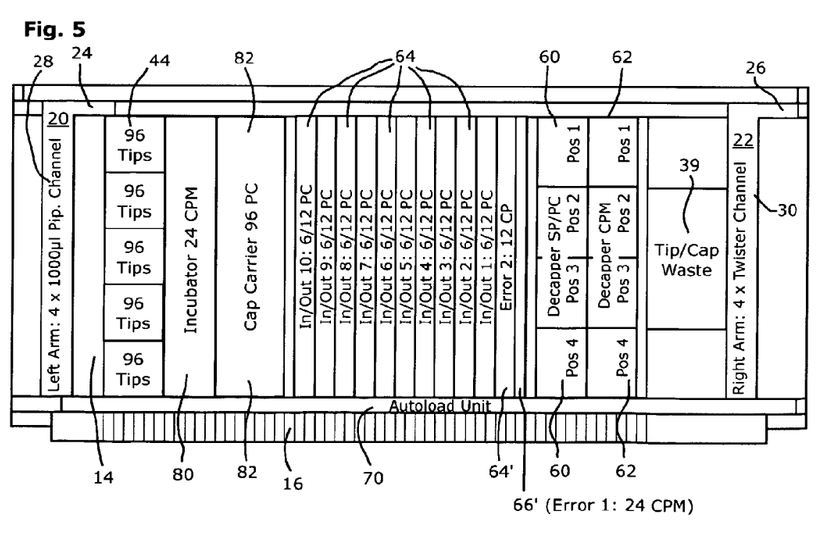
FIG. 5 shows in a schematic and simplified top view another configuration of the sample processing system for a processing method for opening/closing of sample containers of different types.

FIG. 5 shows a configuration for opening/closing of sample containers similar to FIG. 4. Here, however, sample containers of a third type are exemplarily considered, from which in one sample container carrier 64 only six exemplars can be placed. For the sample containers of the first type (SP) and the third type (PC) preferably the same sample container carriers 64 may be used. However, instead of 12 sample containers of the first type (SP) only six sample containers of the third type (PC) may be accommodated, respectively, i.e. between two neighbouring sample container of the third type (PC) exists a free space. With the illustrated configuration it is possible to open up to 60 sample containers of the third type (PC) or to close them with unused closing elements suitable for this type of sample container. The process is the same as described above with respect to FIG. 4 for the therein described sample containers of the first and the second type.

In processing methods for which by means of the sample processing system only an opening or closing of sample containers has to be performed, normally no pipetting tips are used and also the optional incubator is not used. Typically, also the first working arm 20, which is illustrated in FIGS. 4 and 5 on the left side in its standby position, with the pipetting devices provided thereon, is not necessary.

In this respect it is conceivable to provide gripping devices also on the first working arm instead of the pipetting devices. This would result in a processing device, which could by means of two working arms and gripping devices attached thereon perform opening/closing of sample containers faster, since the processing steps to be performed have not been carried out from one working arm with gripping devices, but could be distributed optimized to both working arms.

Figure 6:
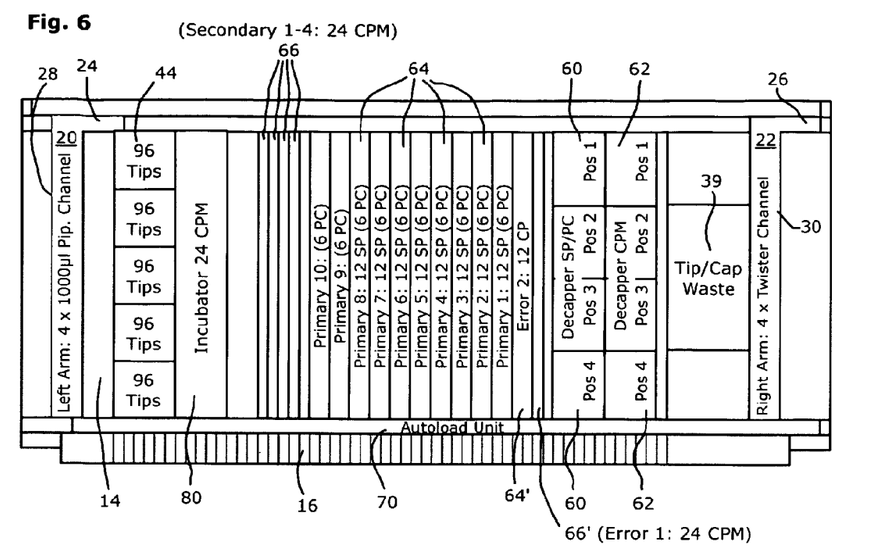
FIG. 6 shows in a schematic and simplified top view a configuration of the sample processing system for a processing method for aliquotation of samples.

FIG. 6 shows a configuration of the sample processing system for performing a method for aliquotation of samples, which are contained in the sample containers. On the loading surface 16 a plurality of sample container carriers 64 with sample containers of a first type (SP) or a third type (PC) are provided. Further, a plurality of sample container carriers 66 for sample containers of a second type (CPM) are provided in the same manner. Finally, also a pipetting tip carrier 44 with a plurality of pipetting tip frames 46 and unused pipetting tips 48 contained therein are provided. The different carriers 44, 64, 66 for sample containers and pipetting tips are moved by means of the loading device 70 into the direction of the receiving plate 14 such that afterwards the sample processing device is filled with carriers 44, 64, 66. As already described above, the carriers and the sample containers or their barcodes may be captured by means of the sensor device 74 of the loading device 70 such that the position of each sample container may be identified uniquely, in particular taking into account in which sample container carrier it is accommodated and at which position of the receiving plate the sample container carrier has been loaded.

Normally, the sample containers of the first (SP) or the third (PC) type contain the entire sample, from which a aliquot has to be taken. These sample containers are typically closed.

In the method a plurality, preferably four, sample containers of the first type are gripped by means of the gripping device 50 on the second working arm 22 and are moved into the direction of the disposal container 39. When the gripping device with the sample containers has arrived there, the sample containers are rotated by the gripping means around the gripper axis of rotation GA, preferably with about 500 to 2000 revolutions per minute, such that the sample in the respective sample containers may be mixed well. After mixing the sample containers are transported to a respective closing device 60 for this type of sample container. After placing and releasing of the closed sample containers their closing elements (preferably screw caps) are detached by means of the closing device 60. The detached closing elements are gripped by the gripping devices and removed from the sample containers, wherein gripping devices perform also a (partial) revolution if necessary to cancel the already detached engagement between the closing element and the sample container. Consecutively, the gripping devices are moved into the direction of the disposal container 39. There, the gripped closing elements are either disposed or they remain in the respective gripping device, to be placed onto the sample container again, later.

By means of the first working arm 20 and a pipetting device 40 attached thereon, pipetting tips (tips) are collected from the corresponding pipetting tip carrier 44.

The pipetting tips are coupled automatically with the pipetting channels of the pipetting devices in this process. The first working arm is then moved into the direction (X) of the closing devices. Each pipetting device is arranged above one sample container accommodated in a respective closing device. Consecutively, the pipetting tips are lowered into the respective sample container to take out (aspire) a specific amount, such as 500 or 1000 µl, of the sample. After aspiring the pipetting devices with the pipetting tips containing the sample liquid are moved to the corresponding sample containers of the second type (CPM) such that an aspirated sample may be delivered (dispensed) into such an up to now empty sample container. After dispensing the first working arm 20 is moved into the direction of the disposal container 39, where the used pipetting tips are ejected and disposed. Then, the first working arm is moved again into the direction of the pipetting tip carrier 44.

The second working arm 22 may now be moved again from its position in the region of the disposal container 39 or its standby position at the right edge, as illustrated in FIG. 6, to the closing devices 60, to be able to place the closing elements holded therein again onto the sample containers within the closing devices. Alternative to reusing of these closing elements, it is also conceivable that these are disposed (into the disposal container 39) and that unused closing elements are collected by means of the gripping devices, for example from a position still left empty in FIG. 6 between incubator and sample container carrier 66 for the sample containers of the second type (CPM). During placing the used or new closing elements the gripping devices may generate a primary relative loose engagement between closing element and sample container, preferably by a (partial) revolution of the closing element with respect to the stationary sample container. Then, the closing elements are left loose by the gripping devices and the closing devices perform the actual closing of the sample containers by tightening of the closing elements. In the following the (re-)closed sample containers may be gripped by the gripping devices and transported back to their position within the sample container carrier and may be placed there. As already described with respect to FIGS. 4 and 5 above, the sample containers may be aligned during placing them again within the sample container carriers by using the sensor device 51 on the gripping device 50. For this alignment process within the configuration presented here it may be assumed that a sample container, whose barcode has been recognized by the sensor device 51, has to be rotated about 160° to 220° around the gripping axis of rotation GA, to align the barcode of the sample container with respect to the direction of the sensor device 74 of the loading device. Of course, according to the arrangement of the two sensor devices 51 or 74 also differing rotation angles are possible or necessary.

After a sample has been extracted in the aforementioned manner from each sample in a sample container of the first (SP) or the third (PC) type and an aliquot is contained in a corresponding sample container of the second type, the different sample container carriers 64, 66 and the pipetting tip carrier 44 may be removed by means of the loading device 70 again from the receiving plate such that they may be taken out again at the loading surface. In particular, the non-closed sample containers of the second type (CPM) with the aliquot are preferably provided to further processing steps, in particular in a neighbouring further processing device for analysis of the biological probe. Within the method for aliquotation of probes described herein, the incubator 80 is not used.

Figure 7:
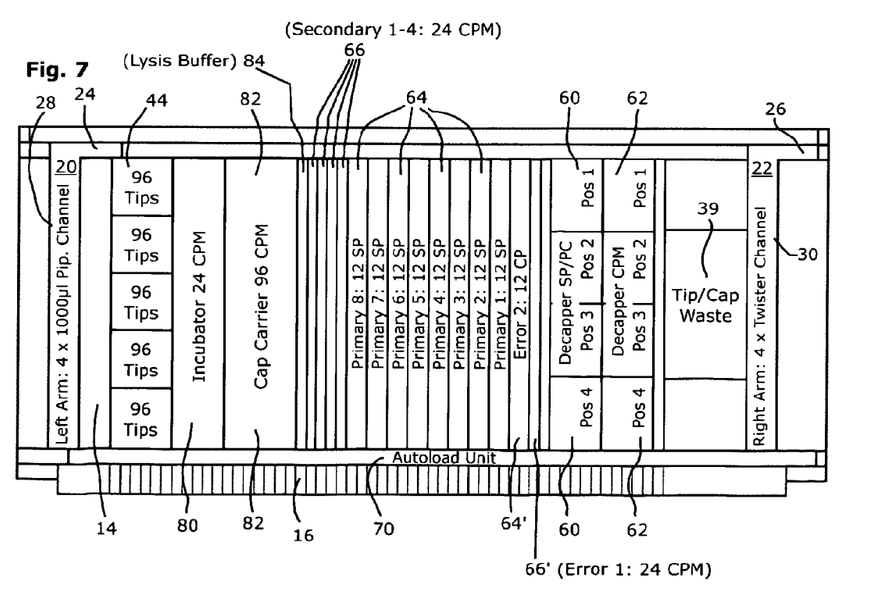
FIG. 7 shows in a schematic and simplified top view a configuration of the sample processing system for a processing method or aliquotation and further processing of samples.

FIG. 7 shows a final configuration, in which additionally to the configuration according to FIG. 6 also a container 84 with a reagent, in particular a lysis-buffer, is provided between the closing element carrier 82 (here for unused closing elements of sample containers of the second type) and sample container carrier 66 for sample containers of the second type (CPM). The reagent, preferably the lysis-buffer, may be added by means of the pipetting devices to the sample containers of the first (SP) or the second (CPM) type such that a mixture of biological probe and reagent may be produced, preferably in the sample containers of the second type. The sample containers of the second type, which comprise a sample aliquot with reagent, may be closed analogously to the method described above. Preferably, the closed containers are then put into the incubator 80, to generate specific chemical reactions within the mixture of sample and reagent. After the desired incubation time the sample containers of the second type may be transported again to the original position in the corresponding sample container carrier 66, wherein, if necessary, the closing elements are removed again beforehands. At the end closed or opened sample containers of the second type with a mixture of probe and reagent may be unloaded, which may be subject to further processing steps, if necessary in a further process device.

Further, in all configurations the sample container carriers 64' and 66' should be noted, which are located on the left side of the closing devices 60, 62 with respect to the figures. These sample container carriers 64' and 66' are empty at the beginning of the different methods and are only filled with sample containers of the respective types, if during processing a problem with a sample container or the sample contained therein occurs. Such problems may for example be: barcode not recognizable, error detected during pipetting or the like.

In the presented methods, which are performed with configurations according to FIG. 6 or FIG. 7, for each sample container of the first or third type a sample container of the second types exists with an identical barcode such that identical samples are also contained in identically marked sample containers. By using two separated sensor devices 51, 73 for reading of barcodes during loading/unloading of sample container carriers and during processing (gripping, mixing, transporting) of the single samples it is possible to capture in an optimal manner which sample container have been loaded, which sample containers have been subjected to which processing steps, and which sample containers have been unloaded again. Obviously, it is also captured, which sample containers have been identified as defective, if necessary, and are located in one of the sample container carriers 64' or 66'.

All configurations or methods have in common that the gripping device is not only used for mere gripping and transporting of sample containers, but that the gripping device(s) is also configured for detecting of barcodes and for alignment of sample containers based on the position, in which the barcode has been read. Further, the gripping device according to the exemplary configurations of FIGS. 6 and 7 may be used as a mixer, without the need to transport and put the sample containers into a special mixing device. All together, according to the proposed sample processing system with one or a plurality of described gripping device(s) optimized processing flows result.

The processing steps described above are performed by means of an accordingly programmed not illustrated control device (computer) of the sample processing system, which is connected with the various components, such as sensor devices, loading device, working arms, pipetting and gripping devices, as well as to their drives such that an according control or regulation of the various components is possible. However, details of the control/regulation are not further detailed here. Also if not every component is mentioned here, which might be controlled by the control device it can nevertheless be assumed that all components, which in any kind contribute actively at method steps to be performed, is connected with the control device.

The invention claimed is:

1. A sample processing system for processing of biological samples, comprising:

a sample processing device
  with a receiving plate,
    wherein the receiving plate is arranged essentially horizontally in a plane defined by a first and a second direction (X, Y);
  with a first and a second working arm,
    wherein the first and second working arm are independently movable along the first direction (X) relative to the receiving plate,
    wherein the first and the second working arm extend essentially in parallel with respect to each other along the second direction (Y) across the receiving plate,
    wherein at least one pipetting device moveable along the second direction (Y) and along a third direction (Z) orthogonal to the first and the second directions (X, Y) is attached to the first working arm,
    wherein at least one gripping device moveable along the second direction (Y) and along the third direction (Z) orthogonal to the first and the second directions (X, Y) is attached to the second working arm,
    wherein grippers provided on the at least one gripping device are rotatable around a gripper axis of rotation (GA) parallel to the third direction (Z); and
  with a control device for controlling the at least one pipetting device and the at least one gripping device;
a plurality of sample containers filled with samples, or fillable with samples or reagents, and
a plurality of pipetting tips usable by means of the at least one pipetting device for aspirating and dispensing a sample or reagents necessary for the sample processing,
wherein the sample containers and the pipetting tips are arranged by means of corresponding sample container carriers and pipetting tip carriers on the receiving plate, respectively,
wherein the control device is configured to mix a sample contained in a sample container by means of the at least one gripping device by rotating a sample container gripped by the grippers around the gripper axis of rotation (GA).

2. The sample processing system according to claim 1, wherein a first sensor device is attached on the at least one gripping device,
  wherein the first sensor device is configured to detect an identification pattern,
  wherein the control device is configured to control the at least one gripping device,
  wherein the at least one gripping device places sample containers into corresponding sample container carriers in a predetermined rotational position relative to respective identification patterns such that the sample containers are or can be aligned with respect to the respective identification pattern.

3. The sample processing system according to claim 1, wherein the sample processing device comprises at least one closing device configured to detach or connect a closing element from or to a sample container.

4. The sample processing system according to claim 3, wherein the control device is configured to deliver or remove open or closed sample containers to/from the closing device by means of the at least one gripping device.

5. The sample processing system according to claim 4, wherein the at least one gripping device is configured to grip and move used closing elements that have been detached from the sample containers or a separated, unused closing element away from the closing device or towards the closing device.

6. The sample processing system according to claim 3, wherein the sample processing device is configured to move the at least one pipetting device towards an opened sample container located within the closing device.

7. The sample processing system according to claim 3, further comprising at least one closing element carrier, by means of which unused closing elements can be or are provided on the receiving plate.

8. The sample processing system according to claim 3, wherein it comprises a disposal container for disposal of used pipetting tips and/or used closing elements.

9. The sample processing system according to claim 3, wherein the at least one gripping device comprises a plurality of moveable grippers, which are configured to grip sample containers or closing elements from the outside.

10. The sample processing system according to claim 1, wherein it further comprises an incubator device,
  wherein said incubator device is arranged on the receiving plate and is capable of accommodating a plurality of sample containers.

11. The sample processing system according to claim 1, wherein it further comprises closure carriers, sample container carriers, and/or further carriers, and a loading device moveable on the receiving plate along the first direction (X),
  wherein the loading device is configured to move pipetting tip carriers, closure carriers, sample container carriers, and/or further carriers necessary for the sample processing along the second direction (Y) towards the receiving plate or away from it.

12. The sample processing system according to claim 11, wherein the loading device comprises a second sensor device to detect an identification pattern of a pipetting tip carrier, a closure carrier, a sample container carrier, and/or a further carrier, and/or to detect an identification pattern of at least one of a sample container accommodated in a sample container carrier.

13. The sample processing system according to claim 1, wherein the number of pipetting devices attached on the first working arm is the same as the number of gripping devices on the second working arm.

14. The sample processing system according to claim 1, wherein on the receiving plate along the first direction (X) are arranged in direction from the first working arm to the second working arm:
  a pipetting tip carrier with a plurality of pipetting tip frames, each arranged next to each other along the second direction (Y);
  at least one sample container carrier for a second type of sample containers;
  at least one sample container carrier for a first or third type of sample container;
  a sample container carrier for sample containers of the first or the third type;
  a sample container carrier for sample containers of the second type; and
  at least one closing device, configured for sample containers of the first and the third type.

15. The sample processing system according to claim 14, further comprising at least one further closing device configured for sample containers of the second type.

16. The sample processing system according to claim 15, comprising a plurality of further closing devices, wherein the plurality of further closing devices are arranged next to each other along the second direction (Y).

17. The sample processing system according to claim 14, comprising a plurality of closing devices,
wherein the plurality of closing devices are arranged next to each other along the second direction (Y).

18. The sample processing system according to claim 1, wherein the plurality of sample containers comprise biological samples.

* * * * *